US010973947B2

(12) United States Patent
Leyendecker (10) Patent No.: US 10,973,947 B2
(45) Date of Patent: Apr. 13, 2021

(54) SURGICAL ADHESIVE INCLUDING HONEY AND METHODS OF PREPARATION AND USE THEREOF

(71) Applicant: Peyton M Leyendecker, Lone tree, CO (US)

(72) Inventor: Peyton M Leyendecker, Lone tree, CO (US)

( * ) Notice: Subject to any disclaimer, the term of this patent is extended or adjusted under 35 U.S.C. 154(b) by 443 days.

(21) Appl. No.: 15/893,654

(22) Filed: Feb. 11, 2018

(65) Prior Publication Data

US 2018/0228935 A1  Aug. 16, 2018

Related U.S. Application Data

(60) Provisional application No. 62/457,256, filed on Feb. 10, 2017.

(51) Int. Cl.
| | | |
|---|---|---|
| *A61L 24/00* | (2006.01) | |
| *A61L 24/06* | (2006.01) | |
| *A61B 17/00* | (2006.01) | |
| *A61J 1/06* | (2006.01) | |
| *A61J 1/20* | (2006.01) | |

(52) U.S. Cl.
CPC .... *A61L 24/0005* (2013.01); *A61B 17/00491* (2013.01); *A61L 24/0015* (2013.01); *A61L 24/06* (2013.01); *A61B 2017/00495* (2013.01); *A61J 1/067* (2013.01); *A61J 1/2093* (2013.01); *A61L 2300/30* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 6,352,704 B1 * | 3/2002 | Nicholson | A61L 24/06 424/400 |
| 2016/0206773 A1 * | 7/2016 | Mousa | A61L 26/0076 |

OTHER PUBLICATIONS

Doun, et al., Tumor Biology, 35:7491. (Year: 2014).*
Ahmed, et al., Evidence-Based Complementary and Alternative Medicine, 2013:1. (Year: 2013).*
Cooper, et al., Eur. J. Clin. Microbiol. Infect. Dis., 20:758. (Year: 2001).*
Dowson, et al., Surg. Laparosc Endosc Percutan Tech, 16:146. (Year: 2006).*
Cerda, et al., Surg. Today, 45:939. (Year: 2015).*

* cited by examiner

*Primary Examiner* — Michael Barker
(74) *Attorney, Agent, or Firm* — Leyendecker & Lemire LLC (57) ABSTRACT

A mixture of honey solution and a surgical adhesive, typically a cyanoacrylate adhesive is described. The adhesive and honey solution are mixed and applied to a cut or wound prior to the cure of the mixture. The adhesive mixture, which retains the strength of the unadulterated adhesive significantly reduces the growth of bacteria in the vicinity of the associated closed cut or wound, has applicability in both human and veterinary medicine.

9 Claims, 9 Drawing Sheets

SURGICAL ADHESIVE INCLUDING HONEY AND METHODS OF PREPARATION AND USE THEREOF

RELATED DISCLOSURES

This application claim priority to and incorporates by reference U.S. Provisional Patent application 62/457,256 filed on Feb. 10, 2017 that has the same title and inventor as the present disclosure.

BACKGROUND

Traditionally, wounds, cuts and incisions of a certain size were closed using stitches. Surgical adhesives have largely supplanted the use of stitches for many types of incisions, cuts and wounds (collectively "cuts"). Studies have shown that when using stitches the skin sometimes doesn't heal normally and deformities can result including the formation of excessive scar tissue. In contrast, when using skin or surgical glue, the skin heals more normally with reduced scarring. Research has shown that the use of surgical adhesives reduces the risk of the closed cut tearing or breaking open. Further, surgical adhesives can be used to form a protective layer over the closed cut reducing the risk of infection when compared to the use of other methods such as stitches or adhesive tape. Nevertheless, infection at a cut site is still a significant risk sometimes necessitating that the associated patient return to a medical care facility for additional care, potentially including additional surgery, to prevent an infection from spreading. Infection at the closed cut can also result in increased unsightly scarring.

The most common type of surgical adhesive are of the cyanoacrylate-type including, but not limited to, n-Butyl cyanoacrylate and 2-Octyl cyanoacrylate. These types of adhesives are notable for curing rapidly in the presence of moisture.

Honey is a sugary food produced by certain insects, such as honey bees, from floral nectar. Honey is largely antimicrobial inhibiting the growth of many if not most microorganisms in or on it. Some studies have indicated that honey can be used effectively to treat and protect wounds and burns. Honey is a supersaturated solution of sugars that has a strong interaction with water molecules. Also, when honey is diluted by a exuding wound, hydrogen peroxide is produced. This is released slowly to provide antibacterial activity. One particular type of honey, Manuka honey, has been used by the indigenous community in New Zealand for centuries because of its healing properties. Manuka honey is produced by honey bees from the nectar of Manuka tree flowers. Studies have attributed the antibacterial properties of Manuka honey to its high osmolality, its hydrogen peroxide content, and its antibacterial phytochemicals.

DETAILED DESCRIPTION

Embodiments of the invention comprise a composition of a honey solution and surgical adhesive typically mixed just prior to application to a cut. Other embodiments pertain to the packaging surgical adhesive with honey solution to be combined just before or contemporaneously with application of the adhesive to a cut or wound. Additional embodiments pertain to the method of mixing and applying the mixture to a cut prior to the cure of the adhesive. Other embodiments pertain to the use of the honey solution modified adhesive on cuts or as a protective layer over cuts or other abrasions to provide protection from infection. The adhesive mixture has applicability in both human and veterinary medicine.

Most simply, the composition comprises a mixture of a surgical adhesive and honey solution that is typically mixed just prior to the application and cure thereof. The honey solution can be of any suitable type but Manuka Honey solution as created by bees from the nectar and pollen of blossoms of the Manuka tree has been found to be advantageous in certain embodiments. The surgical adhesive used can be of any suitable type but typically comprises a cyanoacrylate adhesive in certain embodiments and more specifically cyanoacrylate adhesive specifically developed for medical use, such as n-butyl cyanoacrylate, n-butyl-2 cyanoacrylate, and 2-octyl cyanoacrylate. Generally, cyanoacrylate adhesives are moisture reactive and most be used relatively quickly after exposure to a moisture source such as air, water, or a water containing substrate. Typically in surgical uses the adhesive cures within seconds of contact with biological skin or tissue.

Embodiments of the invention comprise different compositions of the mixture as varying the proportion of honey solution effects both strength and antibacterial properties. For instance, an embodiment comprising a mixture of about 30% honey solution and 70% adhesive may be used wherein maximum shear and adhesive strength is the overarching consideration. However, where bacterial resistance and antibacterial properties are deemed most important, an embodiment comprising a mixture of 80% honey solution may be used.

Because honey solution has a high water content, the adhesive is typically mixed with the honey solution in the desired proportion just prior to application. Interestingly and counter intuitively, cyanoacrylate does not immediately cure when brought into contact with honey solution, which is in sharp contrast to the behavior of the same adhesive when brought into contact with biological skin and tissue. Speculatively, the water in the honey solution, which in supersaturation with sugar is largely unavailable to react with the adhesive. It is still recognized and believed nevertheless that the adhesive does still react with moisture in the air and some free water molecules in the honey solution so use relatively soon after mixing (typically within a couple of minutes or less) is recommended depending on the particular properties of the honey solution utilized in an embodiment.

Embodiments of the honey-modified surgical adhesive can be used in a similar manner as unadulterated surgical adhesives but through the addition of 5-80% honey solution by volume in relation to the amount of adhesive, the antibacterial properties of the combination are greatly enhanced. Advantageously, the risk of bacterial infection at a wound site can be dramatically reduced. Upon adhesive cure, the honey is incorporated into embodiments of the cured adhesive presumably becoming part of the cured polymeric adhesive solid. The resulting solid is typically not tacky and exhibits good flexibility enhancing its ability to remain secured to skin or flesh despite repeated flexing and movement of the substrate. Advantageously, embodiments can be employed as a protective coating over a wound or closed cut to further protect it from infection, promote healing and minimize scarring.

In one method embodiment of using the mixture, the honey solution and adhesive are separately measured either by weight or volume. Next, the two materials are mixed in a suitable container, such as a Petri dish, using a spatula or other suitable mixing implement. Finally, the well mixed composition is applied to a wound wherein it cures rapidly. As can be appreciated, the term "wound" can comprise many things including but not limited to a cut caused by injury, a surgical cut intentionally made, and an abraded or burned skin surface.

In another method embodiment of using the mixture, the honey solution and adhesive are provided or placed in a dual chambered syringe. Typically, the sizes of the two chambers can differ such that when the dual plunger is depressed, the material is dispensed in the desire proportion. For instance wherein a ratio of 2:1 is desired the one chamber will have a cross-sectional area that half that of the other chamber. Typically a mixing spout is provided on the distal ends of the chamber that will mix the two components as they are dispensed from the chamber. The mixture can be applied directly to the wound or metered out on to a intermediate surface for subsequent application. As can be appreciated, a related embodiment comprises the honey solution, the adhesive and the dual chambered syringe wherein the honey solution and the adhesive are each contained in separate chambers. This embodiment may be provided prepackaged and ready for use by merely removing or puncturing seals and securing the mixing nozzle to the distal ends of the chambers.

In yet another method embodiment of using the mixture, the honey solution and adhesive are provided in a flexible foil and/or plastic packet having two chambers separated by a plastic and/or foil membrane that is typically thinner and/or weaker than the remainder of the packet. The user punctures the separating membrane and mixes the honey solution and adhesive, such as by kneading the packet. Once sufficiently mixed. the packet is torn or cut at a nozzle location and applied as desired. As can be appreciated, a related embodiment comprises the honey solution, the adhesive contained and provided in the contained packet in predetermined ratios.

In a fourth method embodiment of using the mixture, the honey solution and adhesive are provided in a dual chambered ampoule or packet in predetermined proportions with each chamber having a separate nozzle. When ready for use the nozzle closures are removed, and the components are dispensed on to a suitable surface, such as a Petri dish. Next, the components are mixed and then applied to a wound as desired. As can be appreciated, a related embodiment comprises the honey solution, the adhesive contained and provided in the described packet or ampoule.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

The phrase "honey solution" as used herein refers to honey mixed with sterile water in any suitable ratio. Typically, water is added to honey to reduce its viscosity to more closely match the viscosity of the surgical adhesive. In variations, the proportion of water added to the honey can vary from 0% to about 60% depending the initial viscosity of the honey.

Embodiments of an Adhesive Mixture of Honey and a Surgical Adhesive.

Broadly, embodiments comprise a surgical adhesive mixed with honey solution, and more specifically, a cyanoacrylate-type adhesive combined with honey solution. The honey solution used in the exemplary embodiment comprises ⅔rds honey to ⅓ sterile water by weight, although other ratios can be used. The relative proportions of the honey solution and surgical adhesive components can vary: preferably about 5-80% of the composition comprises honey solution; more preferably about 15-70% of the composition comprises honey solution; and even more preferably about 25-60% of the composition comprises honey solution all in relation to the proportion of adhesive by volume.

The cyanoacrylate adhesive used in some embodiments can comprise a n-Butyl-2 Cyanoacrylate, such as Histoacryl® topical skin adhesive produced by TissueSeal, LLC of Ann Arbor, Mich. Like other cyanoacrylate adhesives it cures in the presence of moisture or water, such as water contained in human tissue. Typical cure times of the adhesive are less than 30 seconds when placed in contact with flesh or skin It is to be appreciated that in other embodiments and other variations other types of cyanoacrylate adhesive can be used in place of this particular formulation.

The honey used in some embodiments can comprise Manuka Honey. The particular honey used in the experiments described herein is Wedderspoon Manuka Honey distributed by Wedderspoon Organic USA of Malvern, Pa., which has a KFactor of 16. Interestingly, despite the high water content of the honey even with added sterile water, the n-Butyl-2 Cyanoacrylate adhesive does not immediately polymerize and cure when brought into contact with the honey solution permitting a user adequate time to mix the components and apply the mixture to a patient's cut. It is to be appreciated that other types of honey can be used in other embodiments and variations.

Figure 1:
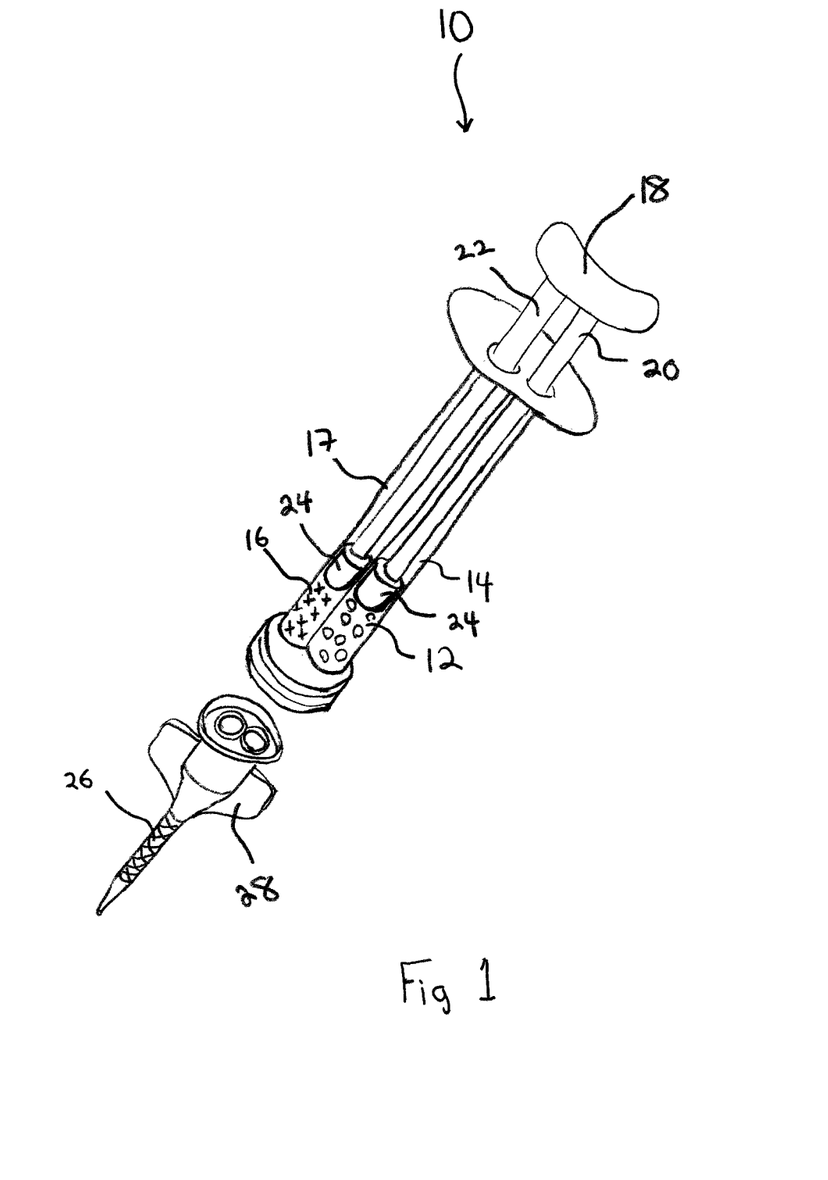
FIG. 1 is an illustration of a first type of delivery system for the honey solution and surgical adhesive mixture comprising a dual chambered syringe and associated mixing nozzle according to one embodiment of the present invention.

Embodiments of a Packaged Combination of Honey and Surgical Adhesive in Predetermined Proportions FIG. 1 comprises a dual chamber syringe 10 in combination with honey solution 12 contained in a first chamber 14 and surgical adhesive 16 contained in the second chamber 17. Each of the respective first and second chambers include proximal and distal ends. A dual shafted plunger 18 is slidably-received through the distal ends with a shaft 20 & 22 being received into each chamber. The distal end of each shaft typically includes a stopper 24 that seals against the adjacent surface of the associated chamber's wall.

Honey solution 12 is contained in one chamber and surgical adhesive 16 is contained in the other chamber. The distal ends of the chamber are sealed to prevent exposure of the adhesive or honey solution to atmosphere until ready for use. A screw-on plastic seal can be used that is removed just prior to use and replaced with a screw-on mixing nozzle 28. As the dual plunger is depressed, the adhesive and honey solution are forced into the mixing nozzle, which includes baffles 26 that churn the materials and cause them to mix together. Upon exiting the nozzle the mixture is ready for use.

Figure 2A:
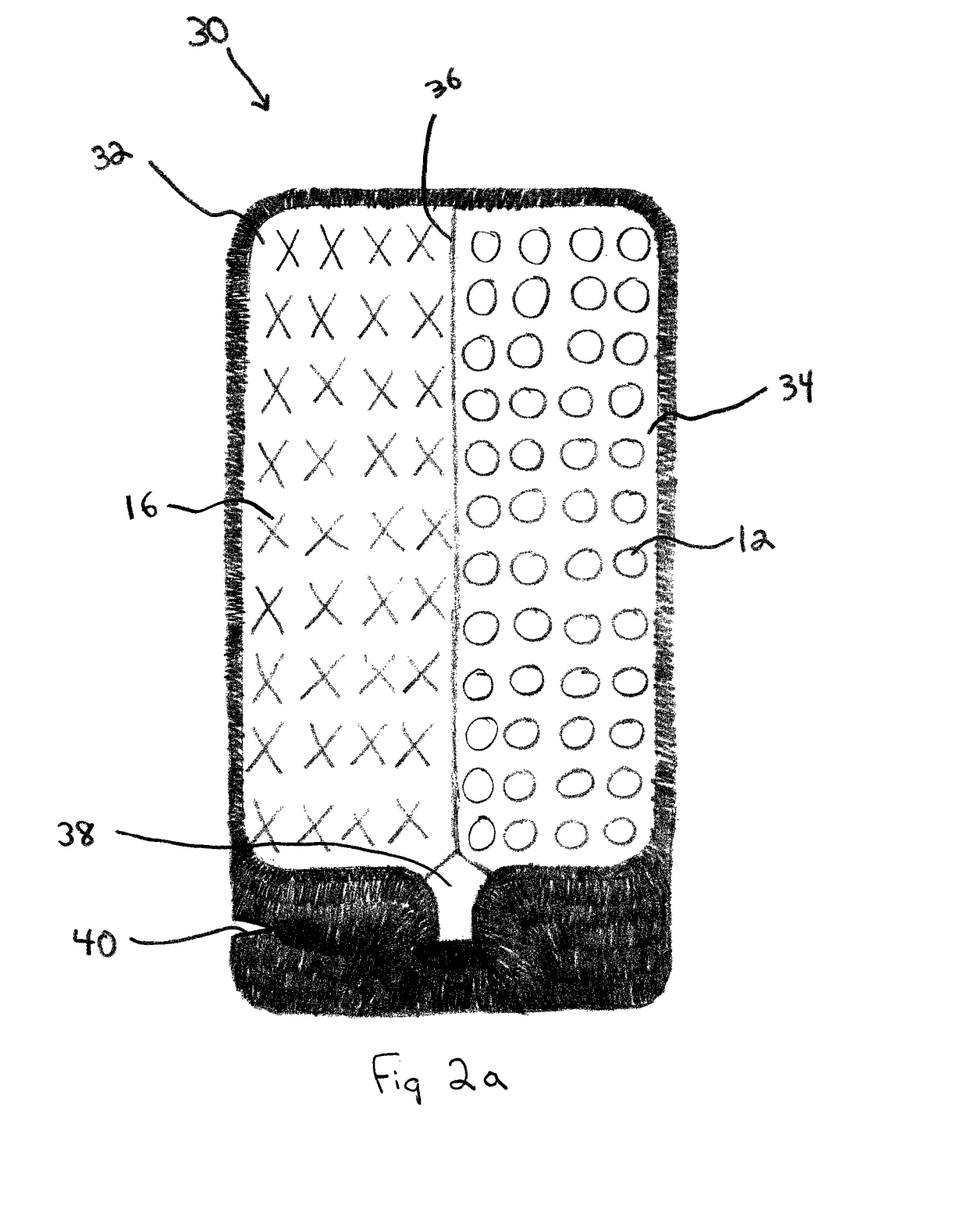
FIG. 2a&b are cross sectional illustrations of a second type of delivery system for the honey solution and surgical adhesive mixture comprising a flexible packet including two chambers separated by a thin membrane according to another embodiment of the present invention.

FIG. 2a is cross sectional illustration of a flexible foil and/or plastic packet 30 defining left and right chambers 32 & 34 separated by a thin membrane 36 that is also typically comprised of plastic. Honey solution 12 is contained in the right compartment and surgical adhesive 16 is contained in the left compartment in desired proportions. A single nozzle orifice 38 is provided through which the contents can be dispensed. the orifice is typically sealed during packet fabrication but a slit 40 may be provided proximate the orifice to permit a user to easily tear it open. In other instances a user can cut the orifice open with scissors or a knife.

Figure 2B:
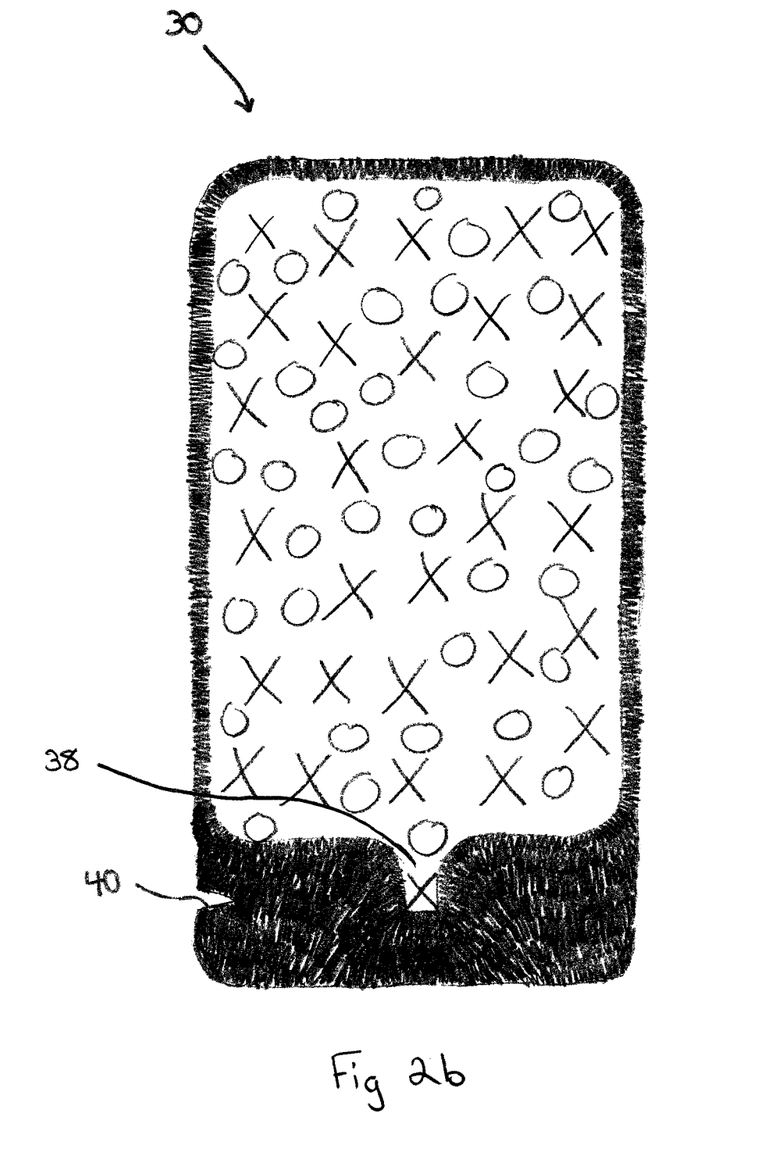

Prior to dispensing, a user punctures the separating thin membrane typically by kneading the packet. Further, kneading mixes the components without exposing them to the atmosphere. Once fully mixed, as shown in FIG. 2b, the orifice 38 is opened and the contents can be dispensed directly onto a wound or cut or squeezed on to an intermediary surface.

As can be appreciated means other than the thin membrane can be used to separate the honey solution and adhesive. For instance, the front and back walls of the packet may be joined in the packet by bond that is easily broken through kneading allowing the contents of the chambers to flow into the other and mix. In yet another version, the packet can comprise a first single chambered packet having a second single chamber packet contained therein along with one of the honey solution and adhesive. The second packet contains the other of the honey solution and the adhesive and can be easily burst to allow a user to squeeze the component in the second packet into the chamber of the first packet and mix the two prior to opening the dispensing orifice of the first packet.

Figure 3:
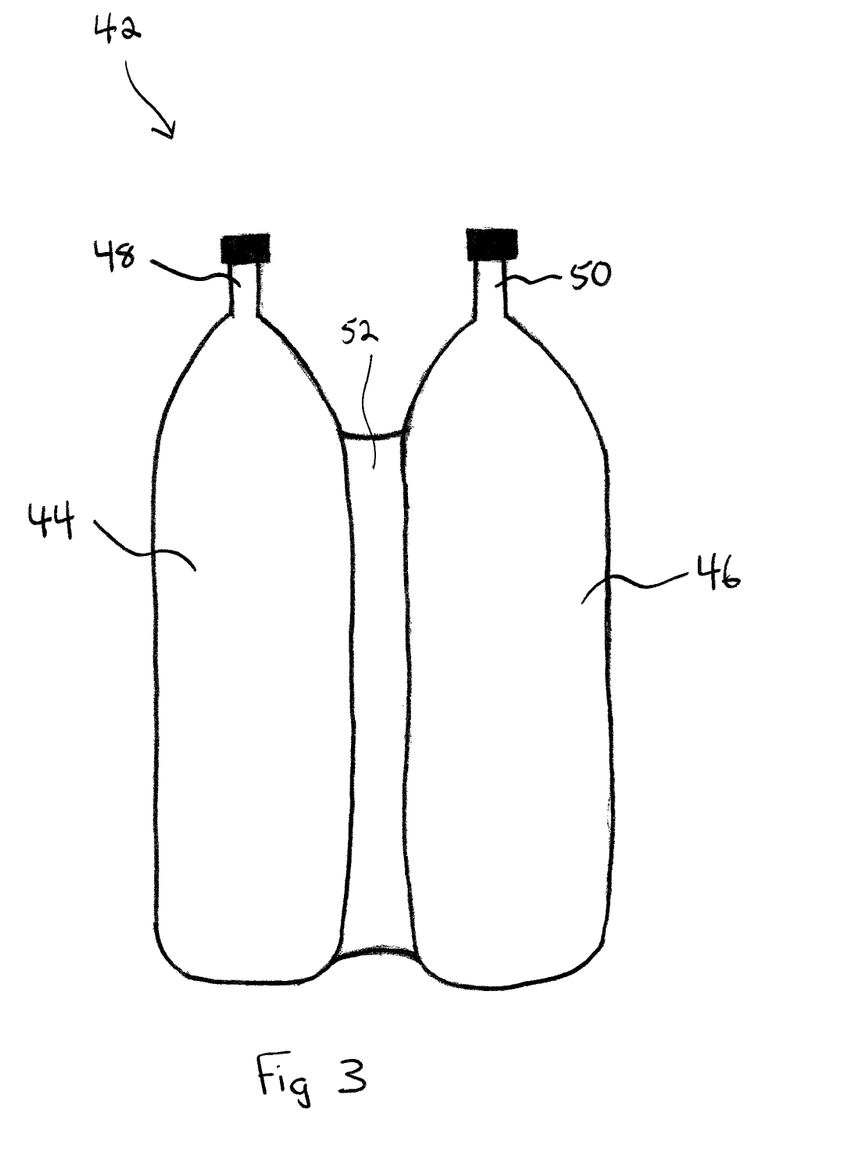
FIG. 3 an illustration of a third type of delivery system for the honey solution and surgical adhesive mixture comprising a dual chamber plastic ampoule according to yet another embodiment of the present invention.

FIG. 3 comprises a dual chambered ampoule 42 that essentially comprises left and right single chambered ampoules 44&46, each with its own dispensing nozzle 48&50, that have been integrally molded and are connected by an attached rib or flange 52. The respective sizes of the chambers can vary to hold the desired proportions of honey solution to adhesive such that measuring is not required prior to use. As can be appreciated instead of plastic ampoules, a flexible foil and/or plastic packet can be provided that has two chambers each with separate dispensing orifices.

In use, the sealed ends of the respective dispensing nozzles are cut off, and the honey solution and adhesive are squeezed on to a suitable mixing surface. The components are mixed and subsequently applied to a cut or wound.

Method Embodiments of Using a Surgical Adhesive and Honey Mixture.

Broadly, the method of preparing and applying the honey modified adhesive comprises the following operations: (1) measuring the desired proportions of each honey solution and adhesive unless the components are provided premeasured in specific packaging; (2) mixing the components together; (3) within a short period of time (generally less than several minutes and preferably under a minute), applying the mixed adhesive to the previously prepped cut or wound; and (4) permitting the adhesive to cure. Optionally, a second layer of adhesive may be applied to the skin surrounding the cut to create a protective layer and inhibit the free growth of bacteria in the region immediately surrounding the cut.

The methods of mixing the components together wherein the honey solution and adhesive are provided premeasured in specific packaging are described in more detail in the proceeding section as pertaining to the type of packaging.

Testing and Experimentation

In experimentation, mixtures of the honey modified adhesive were prepared in various proportions by volume. Volumetric ratios of 1:4, 2:1, 1:1, 1:2 and 4:1 of honey solution to adhesive were mixed by various means. The honey solution used in testing comprised ⅔rds honey to ⅓ sterile water by weight. Testing was performed to determine the effect the addition of honey solution had on the resulting strength of the bond made using the mixture. Simulated cuts or wounds were also made in pork cutlets that were subsequently closed with the mixture. After a predetermined amount of time, the samples were test for bacterial growth. Appropriate control samples were also prepared using unadulterated (or neat) adhesive. Multiple samples were tested for strength and bacterial growth for each proportion.

Figure 4:
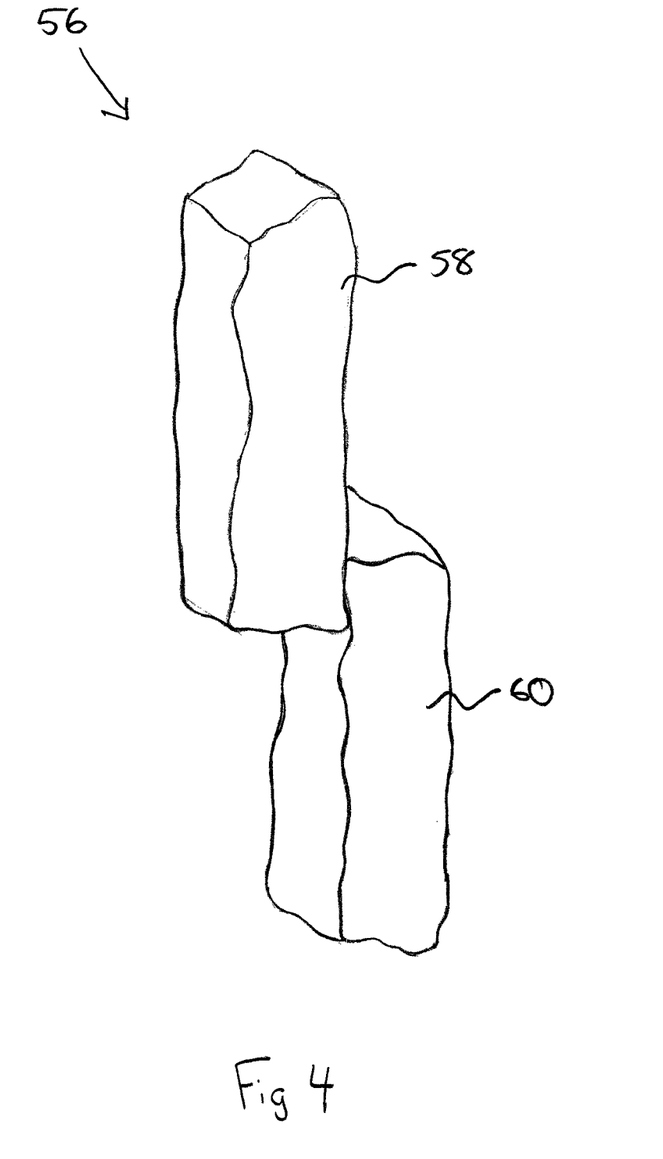
FIG. 4 is an illustration of a lap shear specimen comprised of pork as used in the testing of the shear strength of the cured adhesive mixture according to embodiments of the present invention.

To test the strength lap shear specimens 56 were prepared from boneless pork cutlets having similar thicknesses. An illustration of a typical lap shear specimen is provided in FIG. 4. Each specimen was about 14 mm wide and top and bottom pieces 58&60 were bonded together with the desired adhesive and honey solution mixture with a 12.7 mm overlap. For each specimen tested, the top end of the top piece was clamped into a test fixture and hung downwardly. A bottom clamp assembly was secured to the end of the bottom piece. The bottom clamp assembly included a cup suspended from the bottom clamp into which weights were methodically added permitting sufficient time between each weight to see if the previously added weight would cause a bond failure. Upon failure, the weight of the bottom clamp assembly and the weights was determined and divided by the bond area to determine a lap shear strength in g/cm2.

Figure 6:
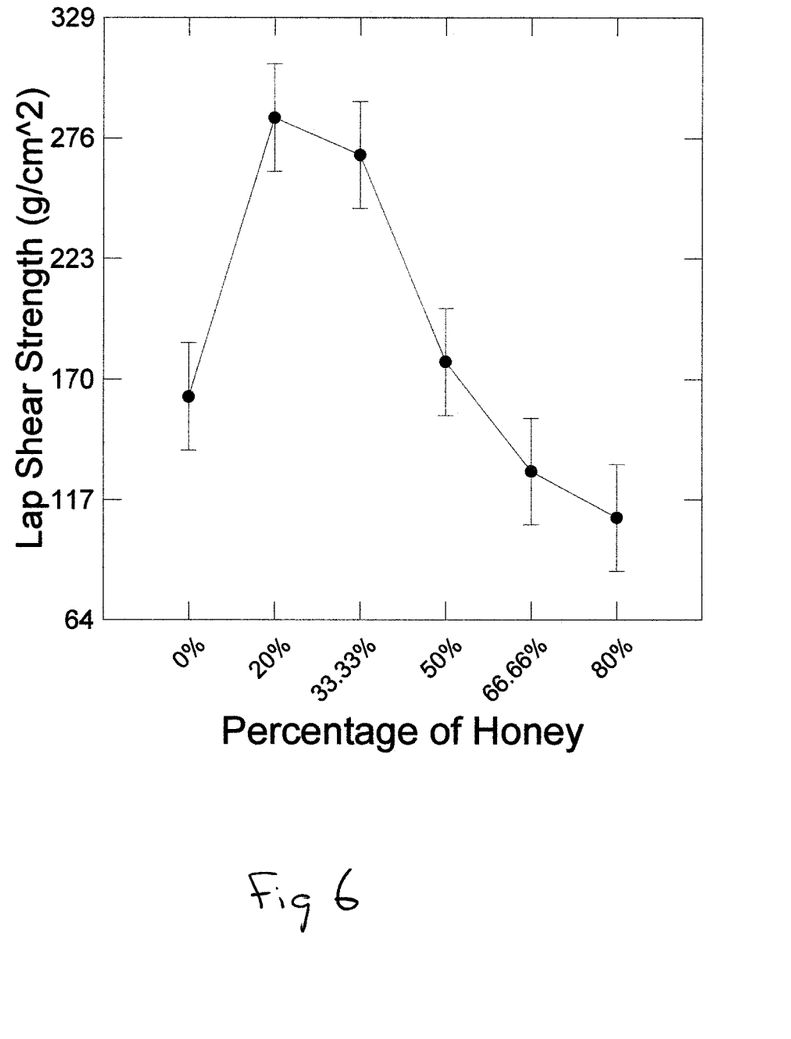
FIG. 6 is a chart illustrating the effect of different concentrations of honey solution on the shear strength of the adhesive mixture according to embodiments of the present invention.

FIG. 6 is a graph illustrating the results of the strength testing. As can be readily seen, the addition of Manuka honey solution to the n-butyl-2 cyanoacrylate adhesive caused a sharp increase in the resulting shear strength compared to the unadulterated adhesive. By using an 80:20 ratio of adhesive to honey solution the shear strength was found to have increased about 75% over adhesive alone. Further, the addition of up to 55% honey solution compared to adhesive offered strengths in excess of the adhesive alone. Even wherein the mixture comprised 80% honey solution, the shear strength of the resulting mixture was about 70% of that of the adhesive alone. The results seem to indicate that the honey solution actively polymerized with the adhesive resulting in a stronger bond with the pork substrate in portions of honey solution of 55% or less. Of note, the resulting cured adhesive solid is not tacky and gives no indication that the honey solution continues you exist separately of the cured adhesive.

Figure 5A:
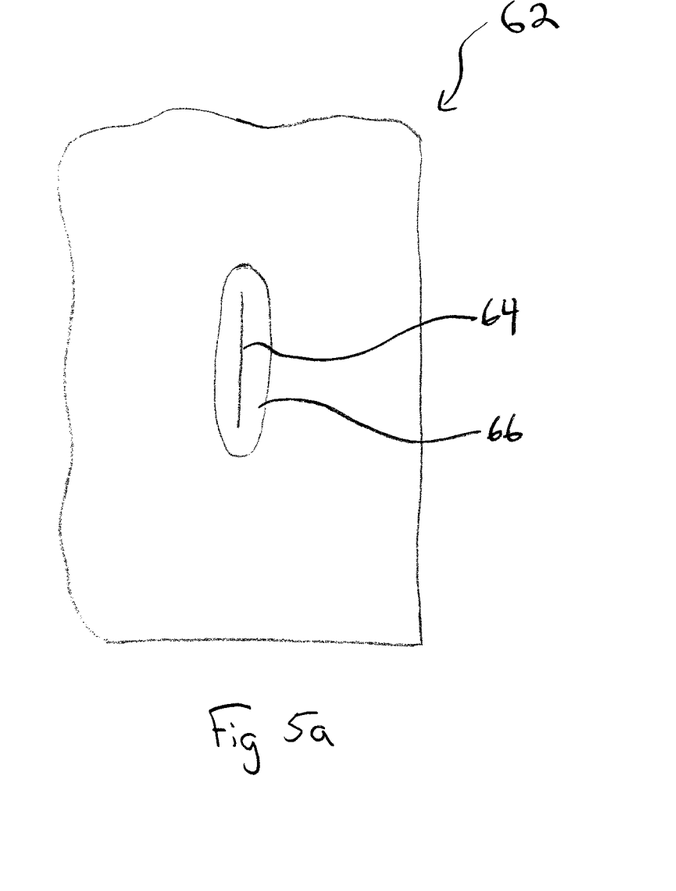
FIG. 5a is illustration of a pork cutlet test specimen having a cut made thereon that is subsequently closed with the adhesive mixture. The cut is later swabbed to determine the relative bacterial concentration on the sealed and repaired cut according to embodiments of the present invention.
Figure 5B:
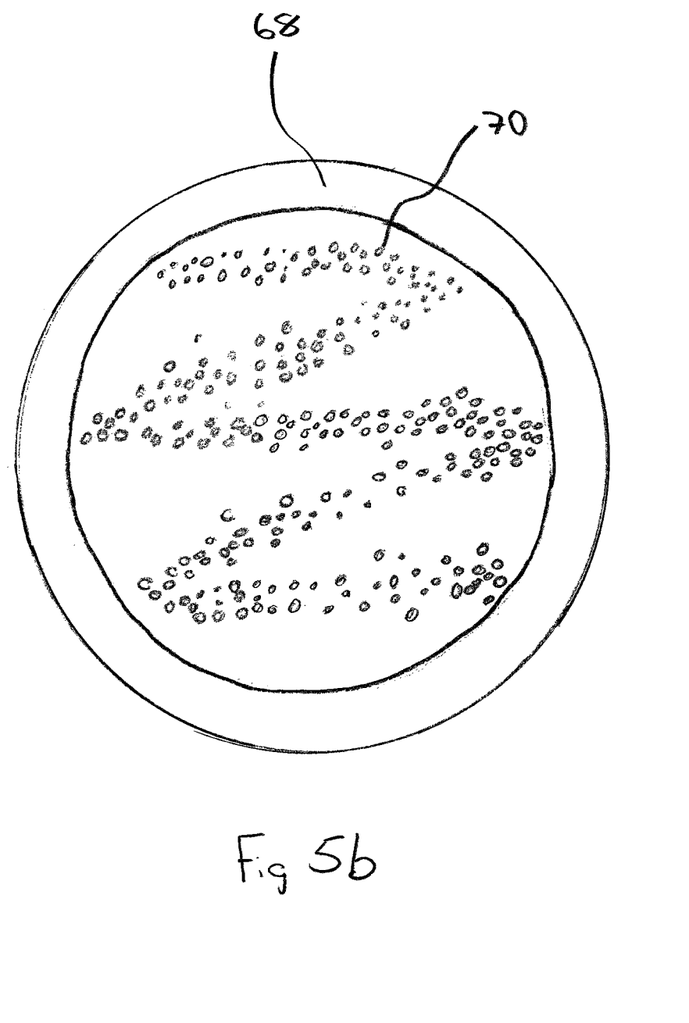
FIG. 5b is an illustration of a Petri dish including an agar substrate in which bacterial colonies were grown from samples taken from the sealed cuts of pork cutlet of FIG. 5a according to embodiments of the present invention.

Bacterial resistance specimens were created by making a cut 64 in a pork cutlet specimen 62 as shown in FIG. 5a. Of note, all specimens for each ratio of adhesive to honey solution were processed and prepared in the same manner to help ensure similar bacterial exposure. Each cut was closed and sealed with an adhesive and honey solution mixture 66 and allowed to sit covered for a period of 24 hours with other specimens of that used mixtures of different ratios. After 24 hours, the adhesive overlying each sealed cut was swabbed to collect bacteria there from and the swabbed contents were transferred to a Petri dish 38 containing sterile agar. Standard laboratory procedures were used. After three days the numbers of bacterial colonies 70 that had grown in each Petri dish as shown in FIG. 5b were counted. Averages counts were determined for each concentration of adhesive to honey solution.

Figure 7:
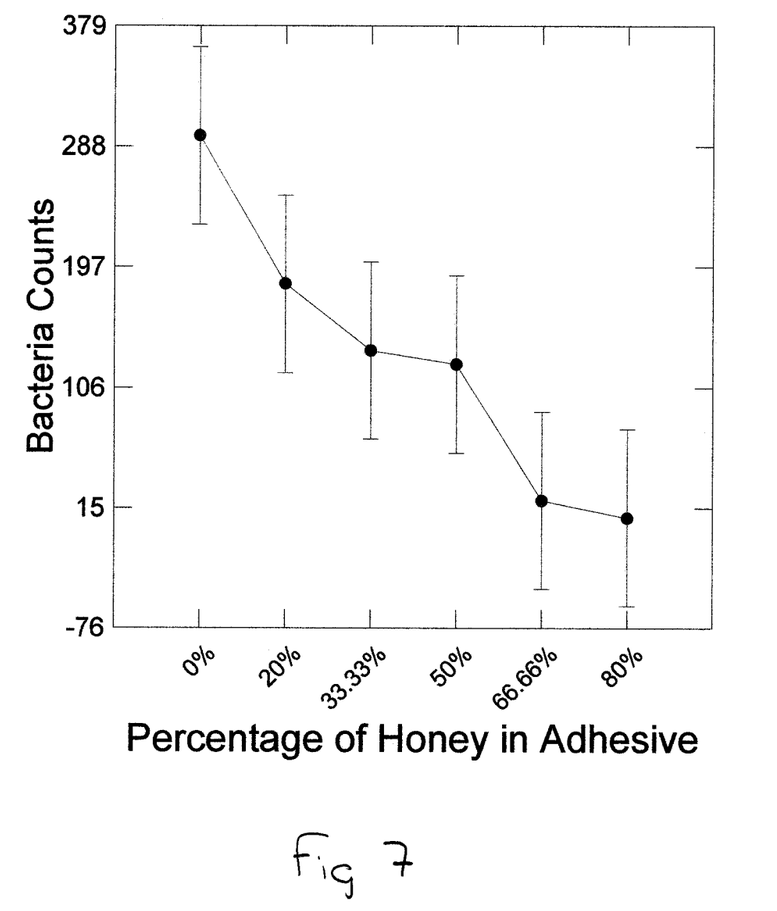
FIG. 7 is a chart illustrating the effect of different concentrations of honey solution on the bacteria count on cuts closed and sealed with the adhesive mixture according to embodiments of the present invention.

FIG. 7 is a graph showing the bacteria counts compared to the percentage of honey solution in the adhesive:honey solution mixture. As can be readily seen, the number of bacterial colonies dropped off in a relatively linear fashion with the addition of greater amounts of honey solution to the adhesive mixture. In an 20:80 ratio of honey solution to adhesive, the bacteria count is reduced by about 40%. Wherein the ratio of honey solution to adhesive is 55:45, a ratio matching the strength of the unadulterated adhesive, the bacterial count is reduced about 70%. Also of significance, wherein a ratio of honey solution to adhesive of 67:33 is used, the bacteria counts are reduced about 90% with only a strength reduction of only about 20% over the unadulterated adhesive.

As can be appreciated, the adhesive mixture can be used in place of the unadulterated surgical adhesive in medical and veterinary applications. The ratio of honey solution to adhesive chosen may differ depending on a particular application. For instance, where the strength of the bond is paramount a mixture with 20-40% honey solution may be used, but in an application where bacteria resistance is most important 50-80% honey solution may be used in the mixture.

Variations and Other Embodiments

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. An adhesive mixture comprising a cyanoacrylate adhesive and honey solution, the honey solution comprising honey and water, wherein (1) the ratio of honey solution to adhesive by volume is between 20:80 and 80:20, (2) the adhesive mixture remains liquid for a period of at least one minute after combination and mixing thereof, and (3) the adhesive mixture cures into a non-tacky solid.

2. The adhesive mixture of claim 1, wherein the adhesive is a n-Butyl-2 Cyanoacrylate adhesive.

3. The adhesive mixture of claim 1, wherein honey in the honey solution is a Manuka Honey.

4. The adhesive mixture of claim 1, wherein honey in the honey solution has a Kfactor of at least 10.

5. The adhesive mixture of claim 1, wherein honey in the honey solution has a Kfactor of at least 15.

6. The adhesive mixture of claim 1, wherein the honey solution comprises two thirds honey to one third water by weight.

7. The adhesive mixture of claim 1, wherein the adhesive mixture cures upon application to a wound site.

8. An adhesive mixture consisting essentially of a cyanoacrylate adhesive and honey solution, the honey solution comprising honey and water, wherein (1) the ratio of honey solution to adhesive by volume is between 20:80 and 80:20, (2) the adhesive mixture remains liquid for a period of at least one minute after combination and mixing thereof, and (3) the adhesive mixture cures into a non-tacky solid.

9. An adhesive mixture consisting of a cyanoacrylate adhesive and honey solution, the honey solution comprising honey and water, wherein (1) the ratio of honey solution to adhesive by volume is between 20:80 and 80:20, (2) the adhesive mixture remains liquid for a period of at least one minute after combination and mixing thereof, and (3) the adhesive mixture cures into a non-tacky solid.

* * * * *